United States Patent
Kuzmanich et al.

(10) Patent No.: US 10,927,057 B1
(45) Date of Patent: Feb. 23, 2021

(54) TWO BED LIQUID PHASE ISOMERIZATION PROCESS

(71) Applicant: UOP LLC, Des Plaines, IL (US)

(72) Inventors: Gregory B. Kuzmanich, Arlington Heights, IL (US); Veronica G. Deak, Chicago, IL (US); Deng-Yang Jan, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/734,474

(22) Filed: Jan. 6, 2020

(51) Int. Cl.
| | |
|---|---|
| *C07C 5/22* | (2006.01) |
| *C07C 5/27* | (2006.01) |
| *B01J 29/70* | (2006.01) |
| *B01J 21/04* | (2006.01) |
| *B01J 21/08* | (2006.01) |
| *C07C 7/09* | (2006.01) |
| *C07C 2/66* | (2006.01) |
| *C07C 7/00* | (2006.01) |
| *C07C 7/12* | (2006.01) |

(52) U.S. Cl.
CPC .............. *C07C 5/2737* (2013.01); *B01J 21/04* (2013.01); *B01J 21/08* (2013.01); *B01J 29/70* (2013.01); *C07C 2/66* (2013.01); *C07C 7/005* (2013.01); *C07C 7/09* (2013.01); *C07C 7/12* (2013.01); *C07C 2529/70* (2013.01); *C07C 2529/80* (2013.01)

(58) Field of Classification Search
CPC .......... C07C 15/02; C07C 2/66; C07C 15/08; C07C 15/00; C07C 6/123; C07C 7/005; C07C 7/12; B01J 29/40; B01J 2229/42; B01J 2229/12; B01J 2229/186; B01J 2229/32; B01J 35/002; B01J 35/023; B01J 35/026; B01J 35/1057; B01J 35/1061; B01J 37/086

See application file for complete search history.

(56) References Cited

U.S. PATENT DOCUMENTS

| | | | |
|---|---|---|---|
| 5,530,170 A | * | 6/1996 | Beck ........................ B01J 29/40 208/135 |
| 9,890,094 B2 | | 2/2018 | Kuzmanich et al. |
| 10,166,532 B2 | * | 1/2019 | Kuzmanich ............. C01B 39/36 |
| 2017/0297977 A1 | | 10/2017 | Bambal et al. |
| 2019/0359542 A1 | * | 11/2019 | Detjen ...................... B01J 29/48 |

* cited by examiner

Primary Examiner — Sharon Pregler

(57) ABSTRACT

A process for ethylbenzene conversion and xylene isomerization of an alkylaromatic feed mixture is described. A $C_8$ alkylaromatic feed mixture can be contacted with two catalyst beds successively in the liquid phase in a $C_8$ aromatic hydrocarbon isomerization zone. The first catalyst comprises a passivated zeolite containing a ten-membered ring channel framework for the conversion of ethylbenzene. The second catalyst comprises UZM-54 zeolite for selective isomerization of the xylenes.

20 Claims, No Drawings

TWO BED LIQUID PHASE ISOMERIZATION PROCESS

BACKGROUND

The xylenes, such as para-xylene, meta-xylene and ortho-xylene, can be important intermediates that find wide and varied application in chemical syntheses. Para-xylene upon oxidation yields terephthalic acid which is used in the manufacture of synthetic textile fibers and resins. Meta-xylene can be used in the manufacture of plasticizers, azo dyes, wood preservers, etc. Ortho-xylene is a feedstock for phthalic anhydride production.

The proportions of xylene isomers from catalytic reforming or other sources generally do not match their demand as chemical intermediates. In addition, the mixture also includes ethylbenzene, which can be difficult to separate or to convert. Typically, para-xylene is a major chemical intermediate with significant demand, but it amounts to only about 20-25% of a typical $C_8$ aromatic stream. The adjustment of an isomer ratio to demand can be effected by combining xylene-isomer recovery, such as adsorption for para-xylene recovery, with isomerization to yield an additional quantity of the desired isomer. Typically, isomerization converts a non-equilibrium mixture of the xylene isomers that is lean in the desired xylene isomer to a mixture approaching equilibrium concentrations.

Various catalysts and processes have been developed to effect xylene isomerization. In selecting an appropriate technology, it is desirable to run the isomerization process as close to equilibrium as practical in order to maximize the para-xylene yield. However, there is a greater cyclic $C_8$ loss due to side reactions associated with such operation. Often, the approach to equilibrium that is used is an optimized compromise between high $C_8$ cyclic loss at high conversion (i.e., very close approach to equilibrium) and high utility costs due to the large recycle rate of unconverted $C_8$ aromatic. Thus, catalysts can be evaluated on the basis of a favorable balance of activity, selectivity, stability, and utility costs.

High ethylbenzene conversions are desired to prevent its accumulation in recycled streams containing $C_8$. To achieve high ethylbenzene conversion, current commercial applications typically operate in the vapor phase which incurs high capital expenditures for heating equipment and a substantial utility load to heat and cool the process streams. One solution to these problems is to operate in the liquid phase. Liquid phase reactions involve substantially lower temperatures, and consequently, lower utility and capital demands. However, current liquid phase based xylene isomerization units suffer from low ethylbenzene conversion, which increases utility costs due to the large recycle rate of ethylbenzene within the system.

Therefore, there remains a need for processes having improved conversion of ethylbenzene and high xylene approach to equilibrium while minimizing loss of xylenes in the liquid phase.

DEFINITIONS

As used herein, the term "zone" can refer to an area including one or more equipment items and/or one or more sub-zones. Equipment items can include one or more reactors or reactor vessels, heaters, separators, exchangers, pipes, pumps, compressors, and controllers. Additionally, an equipment item, such as a reactor or vessel, can further include one or more zones or sub-zones.

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals. The stream can also include aromatic and non-aromatic hydrocarbons. Moreover, the hydrocarbon molecules may be abbreviated $C_1, C_2, C_3 \ldots C_n$ where "n" represents the number of carbon atoms in the hydrocarbon molecule.

As used herein, the term "aromatic" can mean a group containing one or more rings of unsaturated cyclic carbon radicals where one or more of the carbon radicals can be replaced by one or more non-carbon radicals. An exemplary aromatic compound is benzene having a $C_6$ ring containing three double bonds. Other exemplary aromatic compounds can include para-xylene, ortho-xylene, meta-xylene and ethylbenzene. Moreover, characterizing a stream or zone as "aromatic" can imply one or more different aromatic compounds. The stream may have minor amounts of non-aromatic components as well (e.g., less than 10%, or less than 5%).

As used herein, the term "support" generally means an inert material used to provide strength to the zeolitic catalyst before the addition of one or more additional catalytically active components, such as a metal, or the application of a subsequent process such as reducing, sulfiding, calcining, or drying. However, in some instances, a support may have catalytic properties and can be used as a "catalyst".

As used herein, the term "non-equilibrium" generally means at least one $C_8$ aromatic isomer can be present in a concentration that differs substantially (defined as a difference of at least 5 mass-% of the total $C_8$ aromatics) from the equilibrium concentration at isomerization conditions. Isomerization converts a non-equilibrium mixture of xylene isomers which is lean in the desired xylene isomer into a mixture which approaches equilibrium concentrations.

DETAILED DESCRIPTION

The present invention provides a process for ethylbenzene conversion and xylene isomerization of an alkylaromatic feed mixture. A $C_8$ alkylaromatic feed mixture can be contacted with two catalyst beds successively in the liquid phase in a $C_8$ aromatic hydrocarbon isomerization zone. The first catalyst comprises a passivated zeolite comprising ten-membered ring channels, such as MFI, MEL, MFI/MEL intergrowth, TUN, IMF, UZM-39, UZM-44, MTT, TON frameworks, or combinations thereof, for the conversion of ethylbenzene. The second catalyst comprises UZM-54 zeolite for selective isomerization of the xylenes. Both beds are run under similar liquid phase process conditions with no heating or cooling between the two beds. This results in lower operating costs and lower capital costs.

Generally, a refinery or a petrochemical production facility can include an aromatics production facility or an aromatics complex. The aromatics complex can include a xylene isomer separation zone, such as a para-xylene separation zone, and a $C_8$ aromatic isomerization zone. The $C_8$ aromatic isomerization zone can receive a stream depleted of at least one xylene isomer, such as para-xylene and/or meta-xylene. The $C_8$ aromatic isomerization zone can reestablish the equilibrium concentration of xylene isomers and convert other compounds, such as ethylbenzene, to molecules easily separated by fractionation. Typically, such a zone can increase the amount of a xylene isomer, such as para-xylene, and the product from the $C_8$ aromatic isomerization zone can be recycled to the xylene isomer separation zone to recover more of the desired isomer.

The xylene isomer, such as a para-xylene or meta-xylene, separation zone can receive an alkylaromatic feed mixture in a line. Typically, the feed mixture may be derived from any of a variety of original sources, e.g., petroleum refining, thermal cracking such as delay coking or catalytic reforming, catalytic cracking of hydrocarbons, coking of coal, or petrochemical conversions in, e.g., a refinery or petrochemical production facility. Preferably, the feed mixture is found in appropriate fractions from various petroleum-refinery streams, e.g., as individual components or as certain boiling-range fractions obtained by the selective fractionation and distillation of catalytically cracked or reformed hydrocarbons.

The xylene isomer separation zone can include multiple zones of adsorption, purification and extraction to produce an extract of a desired isomer, such as para-xylene, and a raffinate. The xylene isomer separation zone may be based on a fractional crystallization process or an adsorptive separation process. An adsorptive separation process can recover para-xylene over about 99% purity by weight, at high recovery per pass. An exemplary xylene isomer separation zone is disclosed in U.S. Pat. No. 6,740,788 B1. The raffinate, which is an effluent from the zone, can be sent to the $C_8$ isomerization zone.

Typically, the raffinate substantially comprises the alkylaromatic feed mixture. The alkylaromatic feed mixture can include isomerizable alkylaromatic hydrocarbons of the general formula $C_6H_{(6-n)}R_n$, where n is an integer of 1-5 and R is $CH_3$, $C_2H_5$, $C_3H_7$, or $C_4H_9$, in any combination suitable for isomerization to obtain at least one more valuable alkylaromatic isomer, such as para-xylene or meta-xylene, in an isomerized product. The feed mixture can include one or more ethylaromatic hydrocarbons containing at least one ethyl group, i.e., at least one R of at least one of the alkylaromatic hydrocarbons is $C_2H_5$. Suitable components of the feed mixture generally include, for example, an ethylbenzene, a meta-xylene, an ortho-xylene, a para-xylene, an ethyl-toluene, a trimethylbenzene, a diethyl-benzene, a triethylbenzene, a methylpropylbenzene, an ethylpropylbenzene, a diisopropylbenzene, or a mixture thereof. Typically, the one or more ethylaromatic hydrocarbons are present in the feed mixture in a concentration of about 2% to about 100%, by weight.

Usually the feed mixture is prepared by removal of para-, ortho- and/or meta-xylene from a fresh $C_8$ aromatic mixture obtained from one or more aromatic-production or aromatic-conversion processes to yield a stream depleted in at least one xylene isomer. A non-equilibrium $C_8$ aromatic feed mixture including xylenes and ethylbenzene being reacted to yield para-xylene is a particularly preferred application. Typically, such a mixture may have an ethylbenzene content in the approximate range of about 0% to about 50%, by weight, an ortho-xylene content in the approximate range of about 10 to about 90%, by weight, a meta-xylene content in the approximate range of about 0 to about 95%, by weight, and a para-xylene content in the approximate range of about 0 to about 10%, by weight. In some embodiments, the aromatic feed mixture may also include some level of $A_9$-$A_{11+}$ aromatics, as well as some amounts of benzene and toluene. The alkylaromatic containing streams such as catalytic reformate with or without subsequent aromatic extraction can be reacted to produce specified xylene isomers and particularly to produce para-xylene. A $C_8$ aromatic feed may contain non-aromatic hydrocarbons, i.e., naphthenes and paraffins, in an amount up to about 30%, by weight. In some embodiments, the isomerizable hydrocarbons consist essentially of aromatics, however, to ensure pure products from downstream recovery processes. Typically, the non-equilibrium alkylaromatic feed mixture is an effluent from a xylene isomer separation zone.

The $C_8$ aromatic isomerization zone of the present invention comprises two catalyst beds containing different catalysts and operating in the liquid phase.

One exemplary application is the isomerization of a $C_8$ aromatic mixture containing ethylbenzene and xylenes. Generally, the alkylaromatic feed mixture has an ethylbenzene content of about 0 to about 50%, by weight, an ortho-xylene content of up to about 55%, by weight, a meta-xylene content of about 20 to about 95%, by weight, and a para-xylene content of up to about 10%, by weight. One example of a typical alkylaromatic feed mixture comprises about 0 to about 15%, or about 0 to about 10% by weight ethylbenzene, about 10 to about 35%, ortho-xylene, by weight, about 50 to about 80%, by weight meta-xylene, and about 0 to about 5% para-xylene, by weight.

As described, the $C_8$ aromatics are a non-equilibrium mixture, i.e., at least one $C_8$ aromatic isomer is present in a concentration that differs substantially from the equilibrium concentration at isomerization conditions. Usually the non-equilibrium mixture is prepared by removal of para-, ortho- and/or meta-xylene from a fresh $C_8$ aromatic mixture obtained from an aromatic production process. Preferably, the non-equilibrium mixture contains less than 5 mass-% para-xylene.

Accordingly, a $C_8$ alkylaromatic feed mixture can be contacted with two catalyst beds successively in a $C_8$ aromatic hydrocarbon isomerization zone. Contacting may be effected using the catalyst in a fixed bed system.

The alkylaromatic feed mixture may be preheated by any suitable heating means to the desired reaction temperature and then passed into a $C_8$ aromatic isomerization zone containing the two catalyst beds. The two catalyst beds may be contained in a single reactor or in separate reactors. The reactants may be contacted with the catalyst bed in either upward-, downward-, or radial-flow fashion. The reactants are in the liquid phase when contacted with the catalyst in both catalyst beds.

The alkylaromatic feed mixture, preferably a non-equilibrium mixture of $C_8$ aromatics, may be contacted with the first catalyst in the first catalyst bed at suitable ethylbenzene conversion reaction conditions. At least a portion of the ethylbenzene is converted into diethylbenzene such that the resulting ethylbenzene conversion reaction mixture has an ethylbenzene content less than the ethylbenzene content of the alkylaromatic feed mixture.

The first catalyst comprises a passivated zeolite containing the ten membered ring zeolitic structure such as MFI framework, including intergrowths with other ten membered ring zeolitic frameworks. Any suitable MFI zeolite can be used. One suitable MFI zeolite has a Si/Al molar ratio of about 150 or less and a crystal size of 250 nm or greater. The first catalyst typically contains about 1 to about 99 wt % passivated MFI zeolite, or about 10 to about 99 wt %, or about 20 to about 99 wt %, or about 30 to about 99 wt %, or about 40 to about 99 wt %, or about 50 to about 99 wt %, or about 60 to about 99 wt %, or about 70 to about 99 wt %, or about 80 to about 99 wt %, or about 90 to about 99 wt %, or about 1 to about 95 wt %, or about 1 to about 90 wt %, or about 1 to about 80 wt %, or about 1 to about 70 wt %, or about 1 to about 60 wt %, or about 1 to about 50 wt %, or about 1 to about 40 wt %, or about 1 to about 30 wt %, or about 1 to about 20 wt %, or about 1 to about 10 wt %.

The MFI zeolite can be passivated by removing the majority of external surface acidity of the zeolite. Typical means to passivate zeolites are well known in the art and generally involve depositing a layer of chemical on the external surface of the zeolite that is unreactive at process conditions. Materials for this layer may be silica, titania, phosphorous, boron, zirconia, or combinations thereof. The passivating agent may be in the form of a solution, emulsion, a liquid, or a gas under the conditions of contact with the zeolite. This material may be added in a single or multiple stages with or without intervening heat treatments. These heat treatments may or may not contain steam. The passivation can take place either before or after the binder addition (if a binder is present). The zeolite may be calcined or uncalcined. The zeolite is comprised of an ammonium-form zeolite, a hydrogen-form zeolite, or a sodium-form zeolite. The method comprises contacting a zeolite suspension comprised of a zeolite and a solvent with a passivating agent in a liquid phase to deposit the agent on external surfaces of the zeolite. The liquid phase is then removed. The zeolite having the passivating agent deposited on external surfaces thereof is dried and may be calcinated, with or without steam. This passivation process is repeated until the desired level of passivation is achieved.

In some embodiments, the first catalyst may optionally include a binder. The binder may be a refractory inorganic oxide binder or clay. Suitable binders include, but are not limited to, alumina, silica, titania, zirconia, clay, or combinations thereof. Non acidic binders, such silica or titanium, are preferred. The binder is generally present in the amount of about 10 to about 90 wt %, or about 10 to about 80 wt %, or about 10 to about 70 wt %, or about 10 to about 60 wt %, or about 10 to about 50 wt %, or about 10 to about 40 wt %, or about 10 to about 30 wt %, or about 10 to about 20 wt %, or about 20 to about 90 wt %, or about 30 to about 90 wt %, or about 40 to about 90 wt %, or about 50 to about 90 wt %, or about 60 to about 90 wt %, or about 70 to about 90 wt %, or about 80 to about 90 wt %.

In some embodiments, the first catalyst may optionally include a metal to facilitate hydrogenation which can decrease xylene loss. This component may be present in the final catalyst in any amount which is catalytically effective. Generally, the first catalyst includes about 0 to about 5% of metal, or about 0.25 to about 3%, or about 0.25 to about 2% by weight of catalyst. The metal component may be incorporated into the catalyst in any suitable manner. Suitable metals include, but are not limited to, metal of Groups VI, VII, or X of the periodic table, such as Re, Pt, Pt-Sn, Pd, Ni, Co, Ru, or Mo. The metals optionally be modified by sulfur.

One example of a suitable first catalyst comprises in about 10 to about 90 wt % passivated MFI catalyst, about 10 to about 90 wt % binder, about 0 to about 5 wt % metal.

The ethylbenzene conversion reaction conditions in the first catalyst bed include a pressure sufficient to maintain the ethylbenzene conversion reaction mixture in the liquid phase. Generally, such conditions include a temperature ranging from about 190° C. to about 350° C., or about 250° C. to about 300° C. Generally, the pressure is greater than about 2 MPa, or about 2 MPa to about 7 MPa, or about 2.5 to 4.25 MPa. Sufficient catalyst may be contained in the isomerization zone to provide a weight hourly space velocity with respect to the alkylaromatic feed mixture of from about 1 to about 15 hr$^{-1}$, or about 1 to about 4 hr$^{-1}$. Optionally H$_2$ is co-fed with alkylaromatic mixtures. The amounts of H2 is at a level greater than 0.1% of ethylbenzene on a molar basis.

The ethylbenzene conversion reaction mixture is passed to the second catalyst bed which contains a second catalyst comprising UZM-54 zeolite for selective isomerization of the xylenes. The UZM-54 zeolite is described in U.S. Pat. Nos. 9,890,094 and 10,155,532, and U.S. application Ser. No. 20170297977, each of which is incorporated by reference. Suitable second catalysts include about 30% to about 90% zeolite by weight, or about 40% to about 90%, about 50% to about 90%, or about 60% to about 90%.

The second catalyst may also optionally comprise a binder and/or a metal. Suitable binders and metals are the same as those described above for the first catalyst.

The first and second catalyst may contain the same binder and metal, or they could have different binders and/or metals. The amounts of the binders and/or metals could also be the same or different.

The reaction conditions are similar to those described above with respect to the first catalyst bed. The ethylbenzene reaction mixture is sent directly to the second catalyst bed without any intervening heating or cooling. The ability to operate both catalyst beds in the liquid phase under the same conditions provides energy savings.

The isomerization reaction mixture can include a concentration of at least one alkylaromatic isomer that is higher than the equilibrium concentration at the isomerization conditions. Desirably, the isomerization reaction mixture is a mixture of one or more C$_8$ aromatics having a concentration of para-xylene that is at a level around the equilibrium concentration at isomerization conditions. In some embodiments, the isomerization reaction mixture has a % para-xylene to total xylene ratio of about 20 to about 24%.

Any effective recovery scheme may be used to recover an isomerized product from the effluent of the reactors. The isomerization reaction mixture leaving the isomerization reactor includes para-xylene is passed to a para-xylene separation unit to generate a para-xylene process stream, and a second stream comprising meta-xylene, ortho-xylene and ethylbenzene. The para-xylene separation unit can comprise an adsorption separation unit, wherein the para-xylene process stream is the extract stream and the second stream is the raffinate stream. The extract stream and raffinate streams can include a desorbent. The extract stream is passed to a fractionation unit to separate the para-xylene from the desorbent on the basis of boiling point. The process can further include passing the raffinate stream to the isomerization reactor. The raffinate stream can also be passed to a second fractionation column to separate the desorbent from the raffinate stream before passing the raffinate stream to the first catalyst bed.

Typically, the loss of xylenes through the reaction in the two catalyst beds is low, generally less than about 2%, by mole, or no more than about 1%, by mole per pass of xylenes in the feed to the reactor.

"Xylene Loss" is defined as "[((Feed para-, meta-, ortho-xylene)-(Product para-, meta-, ortho-xylene))/(Feed para-, meta-, ortho-xylene)*100%]", which represents material that has to be circulated to another unit in an aromatics complex. Such circulation is expensive, and a low amount of xylene loss is preferred. A$_{11+}$represents material that is heavier, and generally not recoverable.

By the term "about," we mean that the number is within 10% of the value, or within 5%, or within 1%.

Example

Catalyst A was a UZM-54 containing catalyst formulated into ⅟₁₆" trilobe extrudate with alumina. There was no metal present on this catalyst.

Catalyst B was a passivated MFI catalyst prepared by performing passivation onto zeolite followed by formulating the passivated MFI into a 1/16" cylindrical extrudate using an alumina binder. Metal was added during extrusion.

Catalyst C was a different passivated MFI catalyst, prepared by performing passivation onto a cylindrical extrudate containing zeolite and silica binder. There was no metal present on this catalyst.

A comparison was made of a single bed isomerization zone with the two bed arrangement of the present invention. The feed contained 7.3 wt % ethylbenzene (EB), 0.7 wt % para-xylene (PX), 70 wt % meta-xylene, and 22 wt % ortho-xylene.

Table 1 shows the operating conditions and results of isomerization.

TABLE 1

|  | Example 1 | Example 2 | Example 3 |
|---|---|---|---|
| Temperature, C. | 280 | 280 | 280 |
| Pressure, psig | 450 | 450 | 450 |
| H2/HC(mol/mol) | 0.3 | 0.3 | 0.3 |
| WHSV Bed A (1/s) | NA | 2.25 | 2.25 |
| WHSV Bed B (1/s) | 18 | 18 | 18 |
| WHSV Total (1/s) | 18 | 2 | 2 |
| PX/X | 23.4 | 23.35 | 23.35 |
| EB Conversion, % | 3.9 | 28.8 | 31.2 |
| Xylene Loss, Wt % | 0.2 | 0.6 | 0.9 |
| A11+, Wt % | 0.02 | 0.03 | 0.04 |

In Example 1, Catalyst A was used to isomerize a para-xylene-lean steam. The feed was passed over a bed of Catalyst A at a WHSV of 18 and 280° C. Catalyst A established equilibrium with low xylene losses, but had minimal ethylbenzene conversion. In Example 2, two catalysts stacked in a sequential configuration within a single reactor were tested with Catalyst B in the first bed followed immediately by Catalyst A. The WHSV for the bed containing Catalyst B was 2.25 and the WHSV for the bed containing Catalyst A was 18. The combined WHSV was 2. In Example 2, xylene equilibrium was re-established with greater than 25% ethylbenzene conversion. In Example 3, two catalysts stacked in a sequential configuration within a single reactor were tested with Catalyst C in the first bed followed immediately by Catalyst A. The WHSV for the bed containing Catalyst C was 2.25 and the WHSV for the bed containing Catalyst A was 18. The total WHSV was 2. In Example 3, xylene equilibrium was re-established with greater than 30% ethylbenzene conversion.

SPECIFIC EMBODIMENTS

While the following is described in conjunction with specific embodiments, it will be understood that this description is intended to illustrate and not limit the scope of the preceding description and the appended claims.

A first embodiment of the invention is a process for ethylbenzene conversion and xylene isomerization of an alkylaromatic feed mixture, comprising contacting the alkylaromatic feed mixture with a first catalyst bed comprising a first catalyst comprising a passivated zeolite comprising 10-member ring channels to selectively convert ethylbenzene to diethylbenzene at ethylbenzene conversion reaction conditions in a liquid phase to produce an ethylbenzene conversion reaction mixture having an ethylbenzene content less than an ethylbenzene content of the alkylaromatic feed mixture; passing the ethylbenzene conversion reaction mixture directly to a second catalyst bed comprising a second catalyst comprising UZM-54 zeolite without intervening heating or cooling, to selectively isomerize xylenes at isomerization conditions in a liquid phase to produce an isomerization reaction effluent. An embodiment of the invention is one, any or all of prior embodiments in this paragraph up through the first embodiment in this paragraph wherein the isomerization reaction effluent has a % para-xylene to total xylene ratio of about 20 to about 24%. An embodiment of the invention is one, any or all of prior embodiments in this paragraph up through the first embodiment in this paragraph, wherein at least one of the first catalyst or the second catalyst further comprises a binder comprising alumina, silica, titania, zirconia, clay, or combinations thereof. An embodiment of the invention is one, any or all of prior embodiments in this paragraph up through the first embodiment in this paragraph wherein the first catalyst is passivated after the binder is added. An embodiment of the invention is one, any or all of prior embodiments in this paragraph up through the first embodiment in this paragraph wherein the first catalyst comprises the zeolite comprising MFI, MEL, TUN, IMF, UZM-39, UZM-44, UZM-54, MTT, TON, or combinations therein. An embodiment of the invention is one, any or all of prior embodiments in this paragraph up through the first embodiment in this paragraph wherein at least one of the first catalyst or the second catalyst further comprises a metal. An embodiment of the invention is one, any or all of prior embodiments in this paragraph up through the first embodiment in this paragraph wherein the metal is present in an amount of 0 to 5 wt % of catalyst. An embodiment of the invention is one, any or all of prior embodiments in this paragraph up through the first embodiment in this paragraph, wherein the first catalyst contains about 30% to about 90% zeolite by weight. An embodiment of the invention is one, any or all of prior embodiments in this paragraph up through the first embodiment in this paragraph, wherein the second catalyst contains about 30% to about 90% zeolite by weight. An embodiment of the invention is one, any or all of prior embodiments in this paragraph up through the first embodiment in this paragraph wherein the ethylbenzene conversion reaction conditions include a pressure sufficient to maintain the ethylbenzene conversion reaction mixture in the liquid phase, and wherein the isomerization reaction conditions include a pressure sufficient to maintain the isomerization reaction mixture in the liquid phase. An embodiment of the invention is one, any or all of prior embodiments in this paragraph up through the first embodiment in this paragraph, wherein the ethylbenzene conversion reaction conditions include one or more of a temperature of about 190° C. to about 350° C. a pressure greater than 2.4 MPa (a); or a weight hourly space velocity of about 1 $hr^{-1}$ to about 15 $hr^{-1}$. An embodiment of the invention is one, any or all of prior embodiments in this paragraph up through the first embodiment in this paragraph, wherein the isomerization reaction conditions include one or more of a temperature of about 190° C. to about 350° C.; a pressure greater than 2.4 MPa; or a weight hourly space velocity of about 10 $hr^{-1}$ to about 50 $hr^{-1}$. An embodiment of the invention is one, any or all of prior embodiments in this paragraph up through the first embodiment in this paragraph wherein the isomerization reaction effluent has an ethylbenzene conversion of at least 20% with a xylene loss of less than 1 wt %. An embodiment of the invention is one, any or all of prior embodiments in this paragraph up through the first embodiment in this paragraph further comprising passing the isomerization reaction effluent to a para-xylene separation unit to generate a para-xylene enriched process stream and a second stream comprising meta-xylene, ortho-xylene, and ethylbenzene. An embodiment of the invention is one, any or all of prior embodiments in this paragraph up through the first embodiment in this paragraph wherein the para-xylene separation process comprises an adsorption separation unit and generates an extract stream comprising para-xylene and desorbent and a raffinate stream comprising meta-xylene and ortho-xylene, wherein the process further comprises passing the extract stream to a fractionation unit to generate a first stream comprising para-xylene and a second stream comprising desorbent; and passing the raffinate stream to the first catalyst bed.

A second embodiment of the invention is a process for ethylbenzene conversion and xylene isomerization of an alkylaromatic feed mixture, comprising passing the alkylaromatic feed mixture to a first catalyst bed to selectively convert ethylbenzene at ethylbenzene conversion reaction conditions in a liquid phase to produce an ethylbenzene conversion reaction mixture having an ethylbenzene content less than an ethylbenzene content of the alkylaromatic feed mixture, wherein the first catalyst bed comprises a first catalyst comprising an MFI zeolite, and wherein the first catalyst contains about 30 to about 90 wt % zeolite; passing the ethylbenzene conversion reaction mixture directly to a second catalyst bed without intervening heating or cooling to selectively isomerize xylenes at isomerization conditions in a liquid phase to produce an isomerization reaction effluent with a % paraxylene to xylene ratio of about 20 to about 24 wt %, wherein the second catalyst bed comprises a second catalyst comprising UZM-54 zeolite; wherein the isomerization reaction effluent has an ethylbenzene conversion of at least 20% with a xylene loss of less than 1 wt %. An embodiment of the invention is one, any or all of prior embodiments in this paragraph up through the second embodiment in this paragraph wherein at least one of the first catalyst or the second catalyst further comprises one or more of a binder comprising alumina, silica, clay, or combinations thereof; or a metal. An embodiment of the invention is one, any or all of prior embodiments in this paragraph up through the second embodiment in this paragraph wherein the ethylbenzene conversion reaction conditions include a pressure sufficient to maintain the ethylbenzene conversion reaction mixture in the liquid phase, and wherein the isomerization reaction conditions include a pressure sufficient to maintain the isomerization reaction mixture in the liquid phase. An embodiment of the invention is one, any or all of prior embodiments in this paragraph up through the second embodiment in this paragraph, wherein at least one of the ethylbenzene conversion reaction conditions include one or more of a temperature of about 190° C. to about 350° C. a pressure greater than 2.4 MPa; or a weight hourly space velocity of about 1 hr$^{-1}$ to about 15 hr$^{-1}$; or the isomerization reaction conditions include one or more of a temperature of about 190° C. to about 350° C.; a pressure greater than 2.4 MPa; or a weight hourly space velocity of about 10 hr$^{-1}$ to about 50 hr$^{-1}$. An embodiment of the invention is one, any or all of prior embodiments in this paragraph up through the second embodiment in this paragraph further comprising passing the isomerization reaction effluent to an adsorption separation unit and generating an extract stream comprising para-xylene and desorbent and a raffinate stream comprising meta-xylene and ortho-xylene, wherein the process further comprises passing the extract stream to a fractionation unit to generate a first stream comprising para-xylene and a second stream comprising desorbent; and passing the raffinate stream to the first catalyst bed.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for ethylbenzene conversion and xylene isomerization of an alkylaromatic feed mixture, comprising:
    contacting the alkylaromatic feed mixture with a first catalyst bed comprising a first catalyst comprising a passivated zeolite comprising 10-member ring channels to selectively convert ethylbenzene to diethylbenzene at ethylbenzene conversion reaction conditions in a liquid phase to produce an ethylbenzene conversion reaction mixture having an ethylbenzene content less than an ethylbenzene content of the alkylaromatic feed mixture;
    passing the ethylbenzene conversion reaction mixture directly to a second catalyst bed comprising a second catalyst comprising UZM-54 zeolite without intervening heating or cooling, to selectively isomerize xylenes at isomerization conditions in a liquid phase to produce an isomerization reaction effluent.

2. The process of claim 1 wherein the isomerization reaction effluent has a % para-xylene to total xylene ratio of about 20 to about 24%.

3. The process of claim 1, wherein at least one of the first catalyst or the second catalyst further comprises a binder comprising alumina, silica, titania, zirconia, clay, or combinations thereof.

4. The process of claim 3 wherein the first catalyst is passivated after the binder is added.

5. The process of claim 1 wherein the first catalyst comprises the zeolite comprising MFI, MEL, TUN, IMF, UZM-39, UZM-44, UZM-54, MTT, TON, or combinations thereof.

6. The process of claim 1 wherein at least one of the first catalyst or the second catalyst further comprises a metal.

7. The process of claim 6 wherein the metal is present in an amount of 0 to 5 wt % of catalyst.

8. The process of claim 1, wherein the first catalyst contains about 30% to about 90% zeolite by weight.

9. The process of claim 1, wherein the second catalyst contains about 30% to about 90% zeolite by weight.

10. The process of claim 1 wherein the ethylbenzene conversion reaction conditions include a pressure sufficient to maintain the ethylbenzene conversion reaction mixture in the liquid phase, and wherein the isomerization reaction conditions include a pressure sufficient to maintain the isomerization reaction mixture in the liquid phase.

11. The process of claim 1, wherein the ethylbenzene conversion reaction conditions include one or more of: a temperature of about 190° C. to about 350° C. a pressure greater than 2.4 MPa (a); or a weight hourly space velocity of about 1 hr$^{-1}$ to about 15 hr$^{-1}$.

12. The process of claim 1, wherein the isomerization reaction conditions include one or more of: a temperature of about 190° C. to about 350° C.; a pressure greater than 2.4 MPa; or a weight hourly space velocity of about 10 hr$^{-1}$ to about 50 hr$^{-1}$.

13. The process of claim 1 wherein the isomerization reaction effluent has an ethylbenzene conversion of at least 20% with a xylene loss of less than 1 wt %.

14. The process of claim 1 further comprising:

passing the isomerization reaction effluent to a para-xylene separation unit to generate a para-xylene enriched process stream and a second stream comprising meta-xylene, ortho-xylene, and ethylbenzene.

15. The process of claim 14 wherein the para-xylene separation process comprises an adsorption separation unit and generates an extract stream comprising para-xylene and desorbent and a raffinate stream comprising meta-xylene and ortho-xylene, wherein the process further comprises:

passing the extract stream to a fractionation unit to generate a first stream comprising para-xylene and a second stream comprising desorbent; and passing the raffinate stream to the first catalyst bed.

16. A process for ethylbenzene conversion and xylene isomerization of an alkylaromatic feed mixture, comprising:

passing the alkylaromatic feed mixture to a first catalyst bed to selectively convert ethylbenzene at ethylbenzene conversion reaction conditions in a liquid phase to produce an ethylbenzene conversion reaction mixture having an ethylbenzene content less than an ethylbenzene content of the alkylaromatic feed mixture, wherein the first catalyst bed comprises a first catalyst comprising an MFI zeolite, and wherein the first catalyst contains about 30 to about 90 wt % zeolite;

passing the ethylbenzene conversion reaction mixture directly to a second catalyst bed without intervening heating or cooling to selectively isomerize xylenes at isomerization conditions in a liquid phase to produce an isomerization reaction effluent with a % paraxylene to xylene ratio of about 20 to about 24 wt %, wherein the second catalyst bed comprises a second catalyst comprising UZM-54 zeolite;

wherein the isomerization reaction effluent has an ethylbenzene conversion of at least 20% with a xylene loss of less than 1 wt %.

17. The process of claim 16 wherein at least one of the first catalyst or the second catalyst further comprises one or more of:

a binder comprising alumina, silica, clay, or combinations thereof; or a metal.

18. The process of claim 16 wherein the ethylbenzene conversion reaction conditions include a pressure sufficient to maintain the ethylbenzene conversion reaction mixture in the liquid phase, and wherein the isomerization reaction conditions include a pressure sufficient to maintain the isomerization reaction mixture in the liquid phase.

19. The process of claim 16, wherein at least one of:

the ethylbenzene conversion reaction conditions include one or more of:

a temperature of about 190° C. to about 350° C. a pressure greater than 2.4 MPa; or a weight hourly space velocity of about 1 hr$^{-1}$ to about 15 hr$^{-1}$; or the isomerization reaction conditions include one or more of: a temperature of about 190° C. to about 350° C.; a pressure greater than 2.4 MPa; or a weight hourly space velocity of about 10 hr$^{-1}$ to about 50 hr$^{-1}$.

20. The process of claim 16 further comprising:

passing the isomerization reaction effluent to an adsorption separation unit and generating an extract stream comprising para-xylene and desorbent and a raffinate stream comprising meta-xylene and ortho-xylene, wherein the process further comprises:

passing the extract stream to a fractionation unit to generate a first stream comprising para-xylene and a second stream comprising desorbent; and passing the raffinate stream to the first catalyst bed.

* * * * *